(12) United States Patent
Garcia Molina

(10) Patent No.: US 10,080,860 B2
(45) Date of Patent: Sep. 25, 2018

(54) SYSTEM AND METHOD FOR DETERMINING TIMING OF SENSORY STIMULATION DURING SLEEP

(71) Applicant: KONINKLIJKE PHILIPS N.V., Eindhoven (NL)

(72) Inventor: Gary Nelson Garcia Molina, Madison, WI (US)

(73) Assignee: Koninklijke Philips N.V., Eindhoven (NL)

( * ) Notice: Subject to any disclaimer, the term of this patent is extended or adjusted under 35 U.S.C. 154(b) by 353 days.

(21) Appl. No.: 15/021,793

(22) PCT Filed: Sep. 19, 2014

(86) PCT No.: PCT/IB2014/064650
§ 371 (c)(1),
(2) Date: Mar. 14, 2016

(87) PCT Pub. No.: WO2015/049613
PCT Pub. Date: Apr. 9, 2015

(65) Prior Publication Data
US 2016/0220783 A1 Aug. 4, 2016

Related U.S. Application Data

(60) Provisional application No. 61/886,277, filed on Oct. 3, 2013.

(51) Int. Cl.
*A61M 21/02* (2006.01)
*A61B 5/048* (2006.01)
(Continued)

(52) U.S. Cl.
CPC .............. *A61M 21/02* (2013.01); *A61B 5/048* (2013.01); *A61B 5/4812* (2013.01);
(Continued)

(58) Field of Classification Search
CPC . A61B 5/04012; A61B 5/4812; A61B 5/4836; A61M 21/02
See application file for complete search history.

(56) References Cited

U.S. PATENT DOCUMENTS

2008/0081941 A1 * 4/2008 Tononi ............... A61N 2/006
600/14
2010/0318007 A1   12/2010 O'Brien
(Continued)

FOREIGN PATENT DOCUMENTS

| EP | 2495005 A1 | 9/2012 |
|---|---|---|
| WO | 2004100766 A2 | 11/2004 |
| WO | 2007047667 A2 | 4/2007 |
| WO | 2008039930 A2 | 4/2008 |
| WO | 2013086212 A1 | 6/2013 |

OTHER PUBLICATIONS

Ngo et al, "Auditory Closed-Loop Stimulation of the Sleep Slow Oscillation Enhances Memory", Neuron 78, May 8, 2013, pp. 1-9.
(Continued)

*Primary Examiner* — Christine H Matthews

(57) ABSTRACT

The present disclosure pertains to a system configured to determine timing of sensory stimulation provided to a subject to increase sleep slow waves during a sleep session. The system generates output signals conveying information related to a sleep stage of the subject during the sleep session with one or more sensors; detects slow wave sleep in the subject based on the output signals; controls one or more sensory stimulators to provide first sensory stimulation to the subject to induce sleep slow waves; determines a representative slow wave; and determines timing of second stimulation provided to the subject, the second stimulation configured to increase sleep slow waves in the subject during the sleep session, the timing determination based on the representative slow wave.

15 Claims, 4 Drawing Sheets

(51) Int. Cl.
*A61B 5/00* (2006.01)
*A61B 5/04* (2006.01)
*A61M 21/00* (2006.01)

(52) U.S. Cl.
CPC ........ *A61B 5/4836* (2013.01); *A61B 5/04012* (2013.01); *A61M 2021/0016* (2013.01); *A61M 2021/0022* (2013.01); *A61M 2021/0027* (2013.01); *A61M 2021/0044* (2013.01); *A61M 2230/10* (2013.01); *A61M 2230/40* (2013.01)

(56) References Cited

U.S. PATENT DOCUMENTS

2011/0040202 A1 2/2011 Luo et al.
2012/0251989 A1 10/2012 Wetmore et al.

OTHER PUBLICATIONS

Ngo et al, "Induction of Slow Oscillations by Rhythmic Acoustic Stimulation", Journal of Sleep Res., 2012, pp. 1-10.
Tononi et al, "Sleep Function and Synaptic Homeostasis", Sleep Medicien Review, vol. 10, 2006, pp. 49-62.
Massimini et al, "Triggering Sleep Slow Waves by Transcranial Magnetic Stimulation", PNAS, vol. 104, No. 20, 2007, pp. 8496-8501.
Colrain, "The K-Comkplex: A 7-Decade History", Sleep, vol. 28, No. 2, 2005, pp. 255-273.
Riedner et al, "Enhancing Sleep Slow Waves With Natural Stimuli", Medicamundi, vol. 54, No. 2, 2010, pp. 82-88.
Schabus et al, "The Fate of Incoming Stimuli Durin NREM Sleep Is Determined by Spindles and the Phase of the Slow Oscillation", Frontiers in Neurology, vol. 3, Article 40, 2012, pp. 1-11.
Massimini et al, "EEG Slow (~1 Hz) Waves Are Associated With Nonstationarity of Thalamo-Cortical Sensory Processing in the Sleeping Human", Journal of Neurophysiology, vol. 89, No. 3, 2003, pp. 1205-1213.
Tobler, "Phylogeny of Sleep Regulation", Principles and Practice of Sleep Medicine, 2010, pp. 77-90.
Kurth et al, "Characteristics of Sleep Slow Waves in Children and Adolescents", Sleep, vol. 33, O. 4, 2010, pp. 475-480.
Riedner et al, "Temporal Dynamics of Cortical Sources Underlying Spontaneous and Peripherally Evoked Slow Waves", Progress in Brain Research, vol. 193, 2011, pp. 201-218.

* cited by examiner

SYSTEM AND METHOD FOR DETERMINING TIMING OF SENSORY STIMULATION DURING SLEEP

CROSS-REFERENCE TO PRIOR APPLICATIONS

This application is the U.S. National Phase application under 35 U.S.C. § 371 of International Application Serial No. PCT/IB2014/064650, filed on Sep. 19, 2014, which claims the benefit of U.S. Application Ser. No. 61/886,277, filed on Oct. 3, 2013. These applications are hereby incorporated by reference herein.

BACKGROUND

1. Field

The present disclosure pertains to a system and method for determining timing of sensory stimulation provided to a subject to increase sleep slow waves during a sleep session 2. Description of the Related Art Systems for monitoring sleep are known. Sensory stimulation during sleep is known. Sensory stimulation during sleep is often applied continuously and/or at intervals that do not correspond to sleeping patterns of a subject. The present disclosure overcomes deficiencies in prior art systems.

SUMMARY

Accordingly, one or more aspects of the present disclosure relate to a system configured to determine timing of sensory stimulation provided to a subject to increase sleep slow waves during a sleep session. The system comprises one or more sensory stimulators, one or more sensors, one or more processors, and/or other components. The one or more sensory stimulators are configured to provide sensory stimuli to the subject during the sleep session. The one or more sensors are configured to generate output signals conveying information related to a sleep stage of the subject during the sleep session. The one or more processors are configured to execute computer program modules. The computer program modules comprise a slow wave sleep detection module, a probing stimulation module, an identification module, a combination module, a stimulation timing module, and/or other modules. The slow wave sleep detection module is configured to detect slow wave sleep in the subject based on the output signals. Slow wave sleep may be and/or include stage N3 sleep (e.g., according to the new denomination), S4 sleep (e.g., according to the former denomination), deep sleep and/or other slow wave sleep. In some embodiments, slow wave sleep, stage N3 sleep, S4 sleep, and/or deep sleep may all refer to the same type of sleep. The probing stimulation module is configured to, responsive to detection of slow wave sleep, control the one or more sensory stimulators to provide first sensory stimulation to the subject to induce sleep slow waves. The identification module is configured to identify individual ones of the induced sleep slow waves based on the output signals (though individual identification is not always necessary). The combination module is configured to determine a representative slow wave. The representative slow wave is determined based on a combination of the identified induced sleep slow waves, an analysis of the output signals (e.g., a time locked average), and/or based on other information. The stimulation timing module is configured to determine timing of second stimulation provided to the subject. The second stimulation is configured to increase sleep slow waves in the subject during the sleep session. The timing determination is based on the representative slow wave.

Another aspect of the present disclosure relates to a method for determining timing of sensory stimulation provided to a subject to increase sleep slow waves during a sleep session with a timing determination system. The system comprises one or more sensory stimulators, one or more sensors, one or more processors, and/or other components. The one or more processors are configured to execute computer program modules. The computer program modules comprise a slow wave sleep detection module, a probing stimulation module, an identification module, a combination module, a stimulation timing module, and/or other modules. The method comprises generating output signals conveying information related to a sleep stage of the subject during the sleep session with the one or more sensors; detecting, with the slow wave sleep detection module, slow wave sleep in the subject based on the output signals; and, responsive to detection of slow wave sleep, controlling the one or more sensory stimulators with the probing stimulation module to provide first sensory stimulation to the subject to induce sleep slow waves. The method may include identifying, with the identification module, individual ones of the induced sleep slow waves based on the output signals. The method includes determining, with the combination module, a representative slow wave, the representative slow wave determined based on a combination of the identified induced sleep slow waves, an analysis of the output signals (e.g., a time locked average), and/or other information; and determining, with the stimulation timing module, timing of second stimulation provided to the subject. The second stimulation is configured to increase sleep slow waves in the subject during the sleep session. The timing determination is based on the representative slow wave.

Still another aspect of present disclosure relates to a system configured to determine timing of sensory stimulation provided to a subject to increase sleep slow waves during a sleep session. The system comprises means for providing sensory stimuli to the subject during the sleep session; means for generating output signals conveying information related to a sleep stage of the subject during the sleep session; and means for executing computer program modules. The computer program modules comprise means for detecting slow wave sleep in the subject based on the output signals and means for, responsive to detection of slow wave sleep, controlling the means for providing sensory stimuli to provide first sensory stimulation to the subject to induce sleep slow waves. The system may comprise means for identifying individual ones of the induced sleep slow waves based on the output signals. The system comprises means for determining a representative slow wave. The representative slow wave is determined based on a combination of the identified induced sleep slow waves, analysis of the output signals (e.g., a time locked average), and/or other information. The system comprises means for determining timing of second stimulation provided to the subject. The second stimulation is configured to increase sleep slow waves in the subject during the sleep session. The timing determination is based on the representative slow wave.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
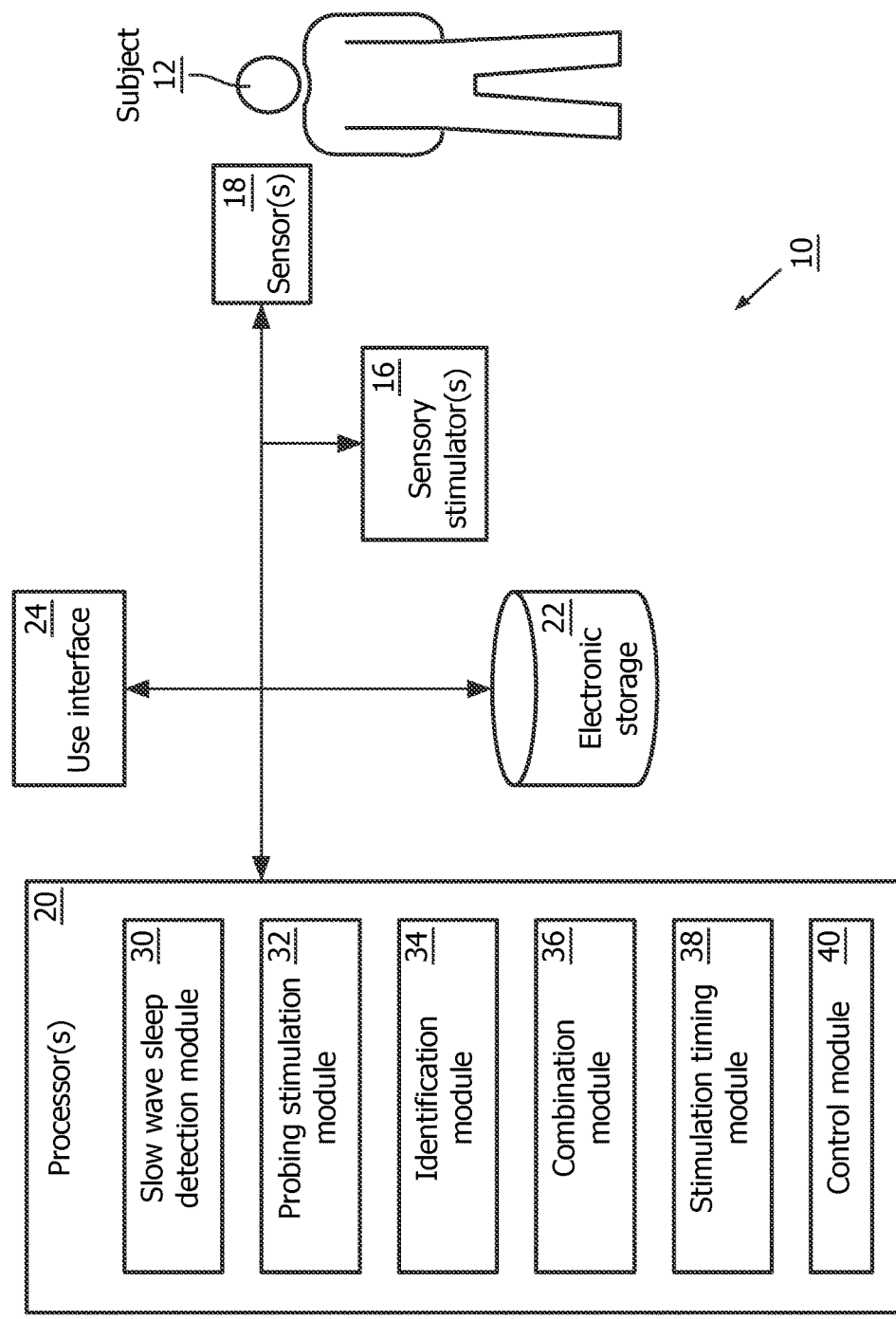
FIG. 1 is a schematic illustration of a system configured to determine timing of sensory stimulation provided to a subject to increase sleep slow waves during a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine timing of sensory stimulation provided to a subject 12 to increase sleep slow waves during a sleep session. Increasing sleep slow waves during a sleep session may cause subject 12 to feel more rested after the sleep session. System 10 is configured to determine a timing for the sensory stimulation provided to subject 12 that approximates the duration of naturally occurring sleep slow waves in subject 12. The duration of sleep slow waves varies from person to person. The duration of sleep slow waves in a single person may change over time (e.g., with age). System 10 is configured to customize the timing of the sensory stimulation for individual users (e.g., subject 12) to increase sleep slow waves in a given user.

System 10 is configured to deliver probing (first) sensory stimulation to subject 12 and then determine a slow wave stimulation timing for subject 12 based on electrical brain activity of subject 12 caused by the probing stimulation. System 10 is configured to deliver slow wave (second) stimulation to subject 12 at the timing determined for subject 12 for the remainder of the sleep session. System 10 may be configured to cease providing the slow wave stimulation one or more times during the remainder of the sleep session if a likelihood of arousal is detected by system 10.

Sleep slow waves are associated with slow wave activity (SWA) in subject 12 during the sleep session. SWA corresponds to the power of an electroencephalogram (EEG) signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated from an EEG for subject 12 during a given sleep session.

The sensory stimuli (probing stimulation and/or slow wave stimulation) may include different types of sensory stimuli. The different types may include odors, sounds, visual stimulation (e.g., lights flashed on open and/or closed eyes), touches, tastes, and/or other types of sensory stimuli. By way of a non-limiting example, system 10 may be configured to deliver acoustic tones to subject 12. In this example, system 10 may be configured to determine an inter tone interval between acoustic tones delivered to subject 12 to increase sleep slow waves. In some embodiments, system 10 may comprise one or more of a sensory stimulator 16, a sensor 18, a processor 20, electronic storage 22, a user interface 24, and/or other components.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices.

Figure 2:
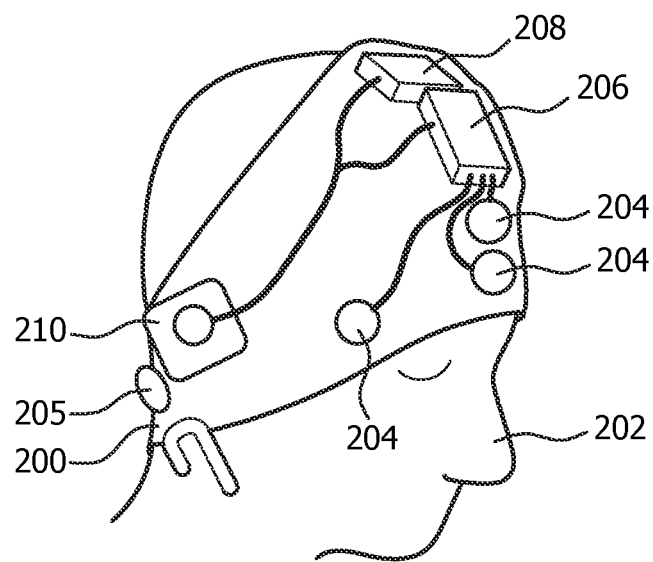
FIG. 2 illustrates a headband worn by a subject.

For example, FIG. 2 illustrates a headband 200 worn by a subject 202. Headband 200 includes sensing electrodes 204, a reference electrode 205, one or more devices associated with an EEG 206, a wireless audio device 208, and one or more audio speakers 210. Audio speakers 210 may be located in and/or near the ears of subject 202. The reference electrode 205 may be located behind the ear of subject 202. In the example shown in FIG. 2, sensing electrodes 204 may be configured to generate output signals conveying information related to the frontal EEG of subject 202, left/right ocular information for subject 202, and/or other information. The output signals may be transmitted to a computing device (e.g., a bedside laptop) wirelessly and/or via wires. Acoustic stimulation may be delivered to subject 202 via wireless audio device 208 and/or speakers 210. An audio signal including information related to auditory stimulation may be generated by the computing device and received by wireless audio device 208. Sensing electrodes 204, reference electrode 205, and devices 206 may be represented, for example, by sensor 18 in FIG. 1. Wireless audio device 208 and speakers 210 may be represented, for example, by sensory stimulator 16 shown in FIG. 1.

Returning to FIG. 1, sensory stimulator 16 is configured to provide sensory stimuli to subject 12. Sensory stimulator 16 is configured to provide sensory stimulation to subject 12 prior to a sleep session, during a sleep session, and/or at other times. For example, sensory stimulator 16 may be configured to provide sensory stimuli to subject 12 during slow wave sleep in a sleep session. Sensory stimulator 16 may be configured to provide sensory stimulation to subject 12 to induce and/or adjust SWA in subject 12. In some embodiments, sensory stimulator 16 may be configured such that inducing and/or adjusting SWA includes inducing, increasing, and/or enhancing sleep slow waves in subject 12.

In some embodiments, sensory stimulator 16 may be configured to induce, increase, and/or enhance sleep slow waves through non-invasive brain stimulation and/or other methods. Sensory stimulator 16 may be configured to induce, increase, and/or enhance sleep slow waves through non-invasive brain stimulation using sensory stimuli. The sensory stimuli include odors, sounds, visual stimulation, touches, tastes, and/or other stimuli. For example, acoustic tones may be provided to subject 12 to induce, increase, and/or enhance sleep slow waves. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to a current sleep stage of subject 12. The current sleep stage of subject 12 may correspond to one or more of non-rapid eye movement (NREM) stage N1, stage N2, or stage N3 sleep, rapid eye movement (REM) sleep, and/or other sleep stages. In some embodiments, NREM stage 3 or stage 2 sleep may be slow wave sleep. Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to a current sleep stage of the subject indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program modules. The one or more computer program modules may comprise one or more of a slow wave sleep detection module 30, a probing stimulation module 32, an identification module 34, a combination module 36, a stimulation timing module 38, a control module 40, and/or other modules. Processor 20 may be configured to execute modules 30, 32, 34, 36, 38, and/or 40 by software; hardware; firmware; some combination of software, hardware, and/or firmware; and/or other mechanisms for configuring processing capabilities on processor 20.

It should be appreciated that although modules 30, 32, 34, 36, 38, and 40 are illustrated in FIG. 1 as being co-located within a single processing unit, in embodiments in which processor 20 comprises multiple processing units, one or more of modules 30, 32, 34, 36, 38, and/or 40 may be located remotely from the other modules. The description of the functionality provided by the different modules 30, 32, 34, 36, 38, and/or 40 described below is for illustrative purposes, and is not intended to be limiting, as any of modules 30, 32, 34, 36, 38, and/or 40 may provide more or less functionality than is described. For example, one or more of modules 30, 32, 34, 36, 38, and/or 40 may be eliminated, and some or all of its functionality may be provided by other modules 30, 32, 34, 36, 38, and/or 40. As another example, processor 20 may be configured to execute one or more additional modules that may perform some or all of the functionality attributed below to one of modules 30, 32, 34, 36, 38, and/or 40.

Slow wave sleep detection module 30 is configured to detect slow wave sleep in subject 12. Slow wave sleep detection module 30 is configured to detect slow wave sleep based on the output signals from sensor 18, and/or other information. In some embodiments, slow wave sleep detection module 30 may identify slow wave sleep in subject 12 based on an analysis of the information conveyed by the output signals. The analysis may include generating and/or monitoring an EEG during a sleep session of subject 12. The EEG may be displayed, for example, by user interface 24. In some embodiments, the analysis may include detecting slow wave sleep based on a ratio that characterizes the depth of sleep. In some embodiments, the ratio may be:

$$\rho = \log\left(\frac{\beta}{\delta}\right),$$

where $\beta$ and $\delta$ represent a power in a beta band (e.g., usually defined as the power in the frequency range 15-30 Hz although variations in limits of the range are very common) of the EEG and a delta band (usually defined as the power in the frequency range 0.5-4.5 Hz although, just as in the case of the beta band, there is no standard definition of the frequency limits) of the EEG respectively. In some embodiments, slow wave sleep detection module 30 is configured to identify slow wave sleep in subject 12 responsive to an instantaneous slow wave sleep ratio $\rho(t)$, estimated based on instantaneous powers $\beta(t)$ and $\delta(t)$, staying below a threshold ratio for longer than a given period of time. In some embodiments, the threshold ratio and/or the given period of time may be determined based on previous sleep sessions of subject 12, and/or other information. In some embodiments, the threshold ratio and/or the given period of time may be programmed at manufacture. For example, the threshold ratio and/or the given period of time may be programmed at manufacture based on empirically accepted values such as a threshold ratio of about −2, and/or a given period of time of about 2 minutes. In some embodiments, slow wave sleep may be detected based on the power level in the alpha band (8-12 Hz) and/or the sigma band (11-15 Hz) in addition to and/or instead of the beta band and the delta band. In some embodiments, slow wave sleep may be detected by other automated processes and/or manually by an operator watching an EEG display, for example.

In some embodiments, slow wave sleep detection module 30 may be configured to identify sleep stages in addition to, and/or instead of slow wave sleep. In some embodiments, slow wave sleep module 32 may be configured to identify a specific sleep stage (e.g., N1, N2, N3, REM, wakefulness) while subject 12 is sleeping.

Probing stimulation module 32 is configured to control sensory stimulator 16 to provide probing sensory stimulation to subject 12 to induce sleep slow waves. Probing stimulation module 32 is configured to control sensory stimulator 16 to provide the probing stimulation responsive to detection of slow wave sleep by slow wave sleep detection module 30. In some embodiments, probing stimulation module 32 is configured such that the probing stimulation comprises three or more individual stimuli delivered to subject 12 with random intervals of time between the individual stimuli. In some embodiments, the probing stimulation comprises four or more individual stimuli. In some embodiments, the probing stimulation comprises five or more individual stimuli. In some embodiments, the random intervals of time between the individual stimuli are at least about two seconds. In some embodiments, the random intervals of time between the individual stimuli are at least about three seconds. In some embodiments, the random intervals of time between the individual stimuli are at least about four seconds.

Typically, an individual slow wave lasts for about one second. A minimum random interval of at least two seconds may ensure that the induced sleep slow waves do not overlap (e.g., the end of a first slow wave does not overlap with the beginning of a second slow wave).

In some embodiments, probing stimulation module 32 may determine other probing stimulation parameters in addition to and/or instead of a quantity of, and a delivery interval for, individual stimuli. For example, for acoustic stimulation, probing stimulation module 32 may determine a tone volume, a tone pitch, and/or other parameters. The probing stimulation may be composed of a sequence of twenty 50-millisecond long acoustic tones having a frequency (pitch) between 500 Hz and 2000 Hz. The volume level of the acoustic tones may be 40 dB. The random inter tone interval between tones may be between three and five seconds.

Figure 3:
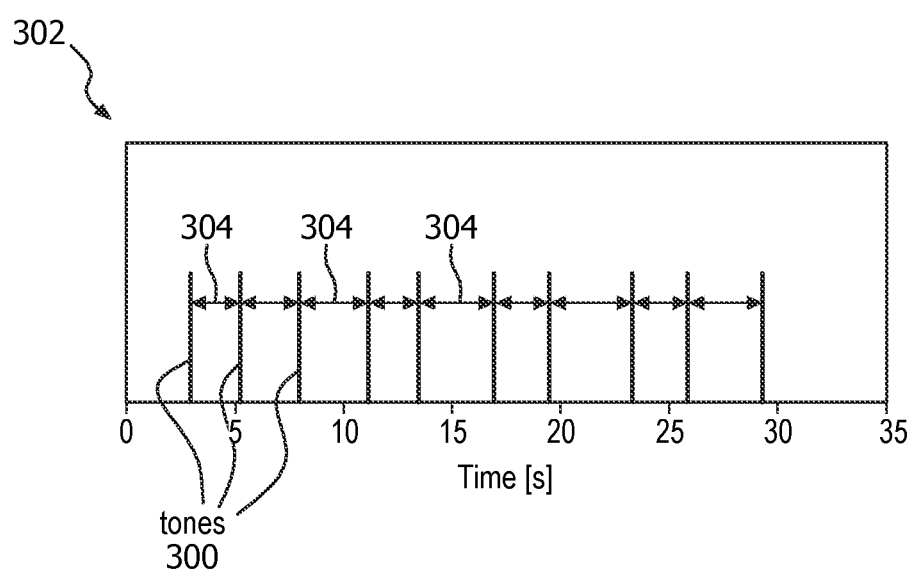
FIG. 3 illustrates a series of acoustic tones delivered as probing stimulation.

FIG. 3 illustrates a series of acoustic tones 300 delivered as probing stimulation 302. The tones 300 have a random inter tone interval 304 of greater than or equal to about two seconds. FIG. 3 illustrates a series of 10 acoustic tones 300. This is not intended to be limiting. The number of tones and/or other individual stimuli used for probing stimulation may be set at manufacture, set and/or adjusted by a user via user interface 24, determined based on previous sleep sessions of subject 12, and/or determined by other methods. A user may include a doctor, a caregiver, subject 12, and/or other users. Changing the number of tones used during the probing stimulation may increase and/or decrease a signal to noise ratio in the EEG. It is known that the increase in signal-to-noise ratio is directly proportional to the square root of the number of tones used during the probing stimulation.

Figure 3A:
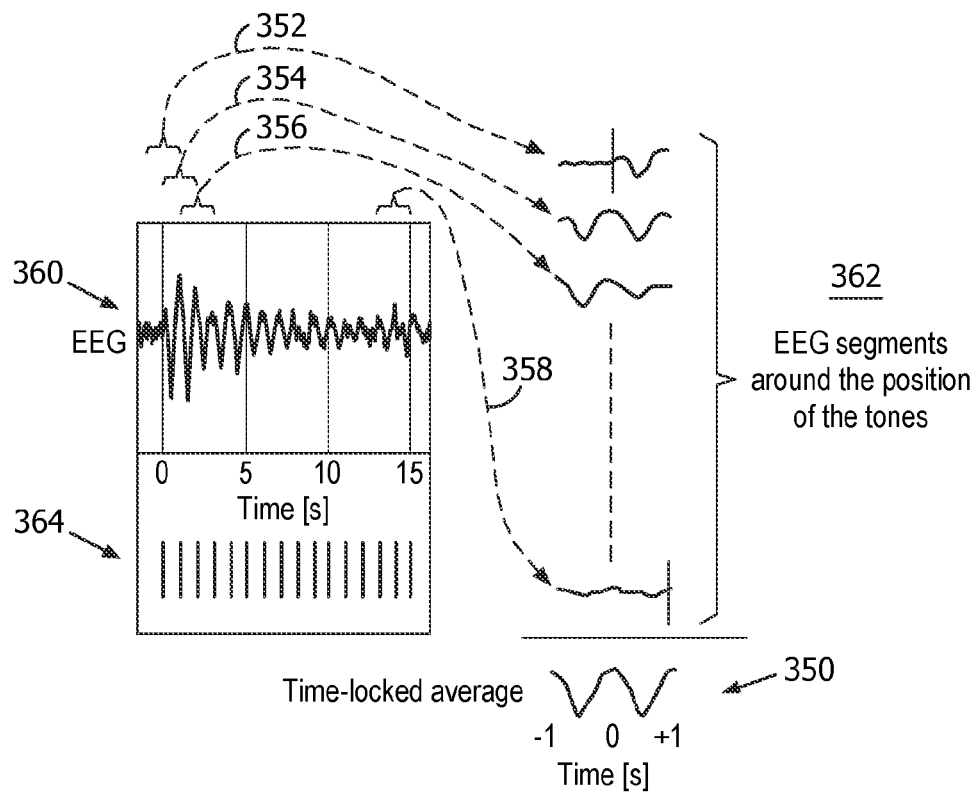
FIG. 3A illustrates a time locked average slow wave.

Returning to FIG. 1, in some embodiments, identification module 34 and/or combination module 36 are configured to perform time locked averaging and/or other operations on the EEG signal (e.g., the EEG generated by slow wave sleep detection module 30). Individual induced slow waves may be aligned in time (with respect to the timing of the individual probing stimuli) and combined (e.g., averaged) to obtain a representative evoked sleep slow wave (e.g., this may be a typical slow wave which has a higher signal-to-noise ratio because of the averaging) which is used to obtain a higher-confidence estimate of the slow wave duration. This typical/representative slow wave has a higher signal-to-noise ratio that is proportional to the square root of the number of tones (for example) in the probing stimulation. The alignment of the slow waves is done according to the timing of the individual stimuli (e.g., tones) in the probing stimulation. The process is illustrated in FIG. 3A. In FIG. 3A, the time locked average refers to a typical and/or representative slow wave 350. Individual portions (e.g., slow waves) 352, 354, 356, and 358 of the EEG 360 are aligned 362 based on the timing of tones 364 played during probing stimulation.

In some embodiments, identification module 34 may be configured to identify individual ones of the induced sleep slow waves (though this is not strictly required). Identification module 34 may be configured to identify the induced sleep slow waves based on the output signals from sensor 18 and/or other information. In some embodiments, identification module 34 may identify individual ones of the induced sleep slow waves based on information related to an EEG (e.g., generated by slow wave sleep detection module 30). Identification module 34 may determine one or more slow wave parameters related to the output signals from sensor 18 (e.g., one or more signals related to the EEG), and/or related to other signals. The one or more slow wave parameters may be related to one or more of a frequency, an amplitude, a shape, a timing, a duration, a phase, and/or other parameters of the output signals from sensors 18, and/or other signals.

Identification module 34 may compare the determined slow wave parameters to one or more predetermined parameter thresholds. Identification module 34 may identify an individual induced sleep slow wave responsive to one or more of the slow wave parameters breaching one or more of the predetermined parameter thresholds. The predetermined parameter thresholds may be determined at manufacture, set and/or adjusted by a user via user interface 24, determined based on previous sleep sessions of subject, and/or determined by other methods. Identification module 34 may be configured to determine the slow wave parameters and/or compare the determined slow wave parameters to the one or more predetermined parameter thresholds one or more times during a sleep session. In some embodiments, identification module 34 may be configured to determine the slow wave parameters and/or compare the determined slow wave parameters to the one or more predetermined parameter thresholds one or more times during a given period of time after the delivery of an individual stimulus during the probing stimulation. In some embodiments, identification module 34 may be configured to determine the slow wave parameters and/or compare the determined slow wave parameters to the one or more predetermined parameter thresholds continuously during the probing stimulation.

By way of a non-limiting example, identification module 34 may determine one or more of a shape, an amplitude, a timing, a phase, and/or a duration of an output signal from a sensor 18 associated with an EEG. In this example, identification module 34 may determine an amplitude of a first electrical activity peak, an amplitude of a second electrical activity peak, a timing of the first peak (e.g., relative to a probing stimulation acoustic tone), a timing of the second peak (e.g., relative to the same acoustic tone), a duration of time between the first peak and the second peak, and/or other slow wave parameters of the EEG signal. Identification module 34 may determine one or more slow wave parameters of the EEG signal during a two second period after the delivery of an acoustic tone that is part of the probing stimulation. Identification module 34 may compare a determined shape, amplitude, timing, and/or duration to predetermined shape, amplitude, timing, and/or duration thresholds. Responsive to a shape, amplitude, timing, phase, and/or a duration of the EEG signal breaching a threshold level, identification module 34 may identify an individual sleep slow wave. The acoustic tone may be one tone in series of tones delivered as probing stimulation by system 10. Identification module 34 may repeat the parameter determination and comparison process during the two seconds that follow additional individual probing stimulation tones.

Combination module 36 is configured to determine a typical/representative slow wave. The typical/representative slow wave is determined based on a combination (e.g., a time locked average) of the identified induced sleep slow waves. Determining the representative slow may include determining one or more representative wave parameters. A given representative wave parameter may correspond to a given slow wave parameter. The given representative wave parameter may be and/or include a combination of the corresponding slow wave parameters determined one or more times for the individual sleep slow waves.

For example, combination module 36 may be configured such that the representative wave parameters include a first electrical activity peak representative amplitude, a second electrical activity peak representative amplitude, a representative timing of the first electrical activity peak, a representative timing of the second electrical activity peak, a representative duration of time between the first electrical activity peak and the second electrical activity peak, and/or other representative parameters. The first electrical activity peak representative amplitude may be determined based on an average and/or other combination of first electrical activity peak amplitudes determined by identification module 34 for the individually identified sleep slow waves. The second electrical activity peak representative amplitude, the representative timing of the first electrical activity peak, the representative timing of the second electrical activity peak, the representative duration of time between the first electrical activity peak and the second electrical activity peak, and/or other representative parameters may be determined by combination module 36 in a similar manner.

In some embodiments, combination module 36 may be configured such that determining a representative slow wave includes a timing based alignment of the individually identified sleep slow waves. The alignment may be based on the timing of the first electrical activity peak relative to the timing of an individual probing stimulus, the timing of the second electrical activity peak relative to the timing of the same individual probing stimulus, and/or other signal wave parameters. For example, the timing of an individual tone that is part of the probing stimulus may be arbitrarily set to "0" seconds on a plot of electrical activity (e.g., in the brain of subject 12) versus time. Plotted lines representing the individually identified sleep slow waves may be overlapped on the electrical activity versus time plot. Representative parameters may be determined based on the overlapped sleep slow waves. Parameters that may be extracted include: the time and amplitude of the first positive peak (see 406 in FIG. 4 described below), the time and amplitude of the negative peak (see 420 in FIG. 4 described below), the time and amplitude of the second positive peak (see 408 in FIG. 4 described below), and/or other parameters.

Figure 4:
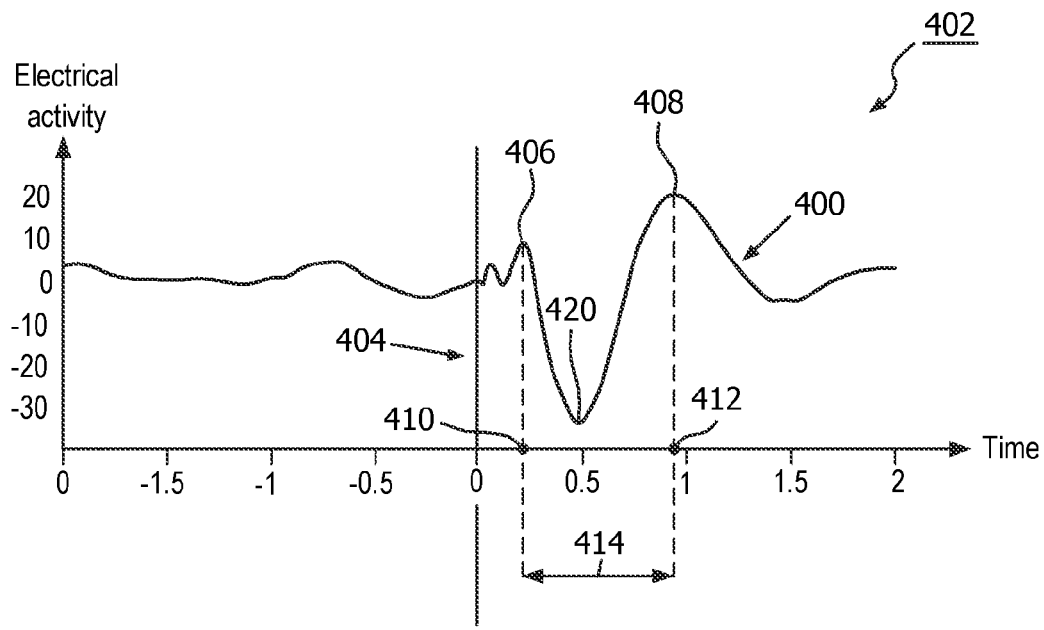
FIG. 4 illustrates a representative slow wave.

By way of a non-limiting example, FIG. 4 illustrates a representative slow wave 400. Representative slow wave 400 is illustrated on a plot 402 of electrical activity versus time. Representative slow wave 400 may correspond to time locked average slow wave 350 shown in FIG. 3A, for example. Representative slow wave 400 is shown relative to the timing 404 of an acoustic tone, for example, provided during probing stimulation. Timing 404 is set to "0" seconds on plot 402. Representative slow wave 400 includes a first electrical activity peak amplitude 406, a negative electrical activity peak 420, a second electrical activity peak amplitude 408, a timing 410 of the first electrical activity peak, a timing 412 of the second electrical activity peak, and a duration of time 414 between first electrical activity peak 406 and second electrical activity peak 408. As described above, parameters 406, 408, 410, 412, 414, and/or other parameters may be determined based on a combination of corresponding slow wave parameters determined by identification module 34 (shown in FIG. 1), determined based on a timing based alignment of the individually identified sleep slow waves, and/or determined by other methods.

Returning to FIG. 1, stimulation timing module 38 is configured to determine timing of slow wave stimulation provided to subject 12. The slow wave stimulation is configured to increase sleep slow waves in subject 12 during the sleep session (e.g., after the probing stimulation has ceased). The timing determination is based on the representative slow wave. In some embodiments, stimulation timing module 38 is configured to determine the timing of the slow wave stimulation based on an amount of time between the first electrical activity peak and the second electrical activity peak (e.g., duration of time 414 shown in FIG. 4) in the representative slow wave (e.g., representative slow wave 400 shown in FIG. 4).

Figure 5:
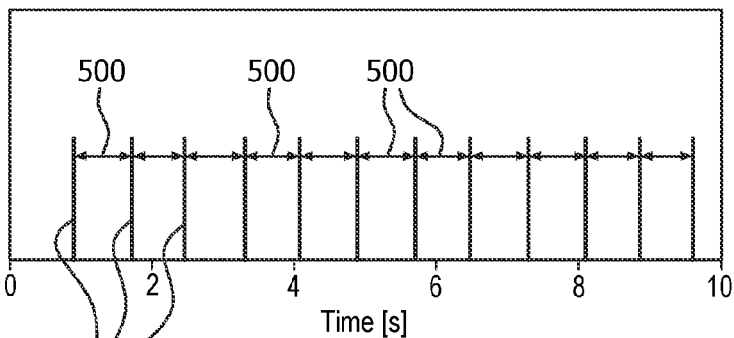
FIG. 5 illustrates a fixed inter tone interval for a series of 12 tones delivered as slow wave stimulation.

In some embodiments, stimulation timing module 38 is configured such that the timing of the slow wave stimulation comprises a regular, repeating interval of time between individual stimuli delivered to subject 12. In some embodiments, stimulation timing module 38 is configured such that the regular, repeating interval of time between individual stimuli (e.g., tones) of the slow wave stimulation is the amount of time between the first electrical activity peak and the second electrical activity peak in the representative slow wave. For example, when the slow wave stimulation includes tones delivered to subject 12, an inter tone interval may be determined by stimulation timing module 38 to be the amount of time between the first electrical activity peak and the second electrical activity peak in the representative slow wave. FIG. 5 illustrates a fixed inter tone interval 500 for a series of 12 tones 502 delivered as slow wave stimulation. Fixed inter tone interval 500 in FIG. 5 may correspond to, for example, duration of time 414 shown in FIG. 4.

Returning to FIG. 1, in some embodiments, stimulation timing module 38 is configured such that the timing of the slow wave stimulation is variable between individual stimuli. In these embodiments, stimulation timing module 38 may be configured such that the timing of the slow wave stimulation is determined based the amount of time between the first electrical activity peak and the second electrical activity peak. The timing of the slow wave stimulation may correspond to a given phase of a sleep slow wave. The given phase may be associated with a slow wave's down state (e.g., negative peak 420 of the slow wave shown in FIG. 4) and/or a slow wave's up state (e.g., generally the second positive peak 408 in FIG. 4). Stimulation timing module 38 may be configured to determine whether the timing of the slow wave stimulation is the amount of time between the first electrical activity peak and the second electrical activity peak and/or is only based on the amount of time between the peaks via information entered and/or selected by a user via user interface 24, instructions programmed during manufacture of system 10, and/or by other methods.

Control module 40 is configured to control sensory stimulator 16 to deliver the slow wave stimulation to subject 12 with the timing determined by stimulation timing module 38. Control module 40 is configured to control sensory stimulator 16 to deliver the slow wave stimulation to subject 12 with the timing determined by stimulation timing module 38 while subject 12 is determined to be in slow wave sleep (e.g., stage N3).

In some embodiments, control module 40 may control sensory stimulator 16 to provide the slow wave stimulation during the sleep session such that the slow wave stimulation does not wake subject 12. For example, control module 40 may control sensory stimulator 16 to provide the slow wave stimulation at a low intensity level. As another example, control module 40 may cause sensory stimulator 16 to deliver acoustic stimulation to subject 12 to increase sleep slow waves with an inter tone interval determined by stimulation timing module 38 while subject 12 is determined to be in stage N3 sleep. Control module 40 may control sensory stimulator 16 to deliver slow wave stimulation to subject 12 during stage N3 sleep because the likelihood for slow-wave induction, and/or increase during the specific sleep stage may be comparatively higher than in other sleep stages, the user may be less likely to be awakened by the slow wave stimuli, and/or for other reasons. In some embodiments, control module 40 is configured to control sensory stimulator 16 to cease providing the slow wave stimulation to subject 12 responsive to slow wave sleep detection module 30 indicating that subject 12 is waking up.

In some embodiments, system 10 is configured such that the operations performed by slow wave sleep detection module 30, probing stimulation module 32, identification module 34, combination module 36, stimulation timing module 38, and/or other modules are performed only once after a first period of slow wave sleep within a sleep session. In these embodiments, control module 40 may control sensory stimulators 16 to deliver the slow wave stimulation at the timing determined by stimulation timing module 38 during individual periods of slow wave sleep for the rest of the sleep session. In some embodiments, control module 40 may control sensory stimulators 16 to deliver the slow wave stimulation at the same timing during periods of slow wave sleep in future sleep sessions of subject 12. The timing determined by stimulation module 38 may be stored in electronic storage 38 and retrieved by control module 40 during future sleep sessions, for example. In some embodiments, control module 40 may cause information related to the sleep session of subject 12 to be stored in electronic storage 22.

In some embodiments, system 10 is configured such that the operations performed by slow wave sleep detection module 30, probing stimulation module 32, identification module 34, combination module 36, stimulation timing module 38, and/or other modules are performed for two or more individual periods of slow wave sleep within a sleep session. In these embodiments, control module 40 may control sensory stimulators 16 to deliver the slow wave stimulation at the most recent timing determined by stimulation timing module 38. Control module 40 may control sensory stimulator 16 to deliver the slow wave stimulation at the most recently determined timing for the corresponding individual period of slow wave sleep until a new timing is determined by stimulation timing module 38, and/or for other periods of time. In some embodiments, system 10 is configured such that the operations performed by slow wave sleep detection module 30, probing stimulation module 32, identification module 34, combination module 36, stimulation timing module 38, and/or other modules are performed every time a slow wave sleep cycle is detected during a sleep session. The time required to deliver the probing stimulation and obtain a customized timing for the slow wave stimulation (e.g., an inter tone interval when the stimulation includes acoustic tones) may be shorter than one minute. Control module 40 may control sensory stimulator 16 to deliver the slow wave stimulation at the most recently determined timing for the corresponding individual period of slow wave sleep until a new timing is determined by stimulation timing module 38 for the next period of slow wave sleep.

By way of a non-limiting example, the probing stimulation may be applied during the first use of system 10 by subject 12. The resulting timing of the slow wave stimulation determined by stimulation timing module 38 may be used by control module 40 for the periods of slow wave sleep during the rest of the sleep session and future sleep sessions of subject 12.

By way of another non-limiting example, the probing stimulation (e.g., lasting for less than a minute) may be applied at the beginning of individual periods of slow wave sleep and the resulting customized inter tone interval (for example) may be used only for the remaining portion of that period of slow wave sleep within the sleep session. The embodiment described in this example may be used when the duration of sleep slow waves (e.g., about one second) varies for individual periods of slow wave sleep in subject 12, for example, when slow wave variations related to age are expected, and/or for other applications.

The frequency with which the operations of slow wave sleep detection module 30, probing stimulation module 32, identification module 34, combination module 36, stimulation timing module 38, and/or other modules are performed may be determined at manufacture, determined based on user input via user interface 24, determined based on previous sleep sessions of subject 12, and/or determined by other methods. The various example frequencies described herein (e.g., once at the first use of system 10, once per period of slow wave sleep, etc.) are not intended to be limiting. The frequency with which the operations described above are performed may be any frequency that allows system 10 to function as described.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 6:
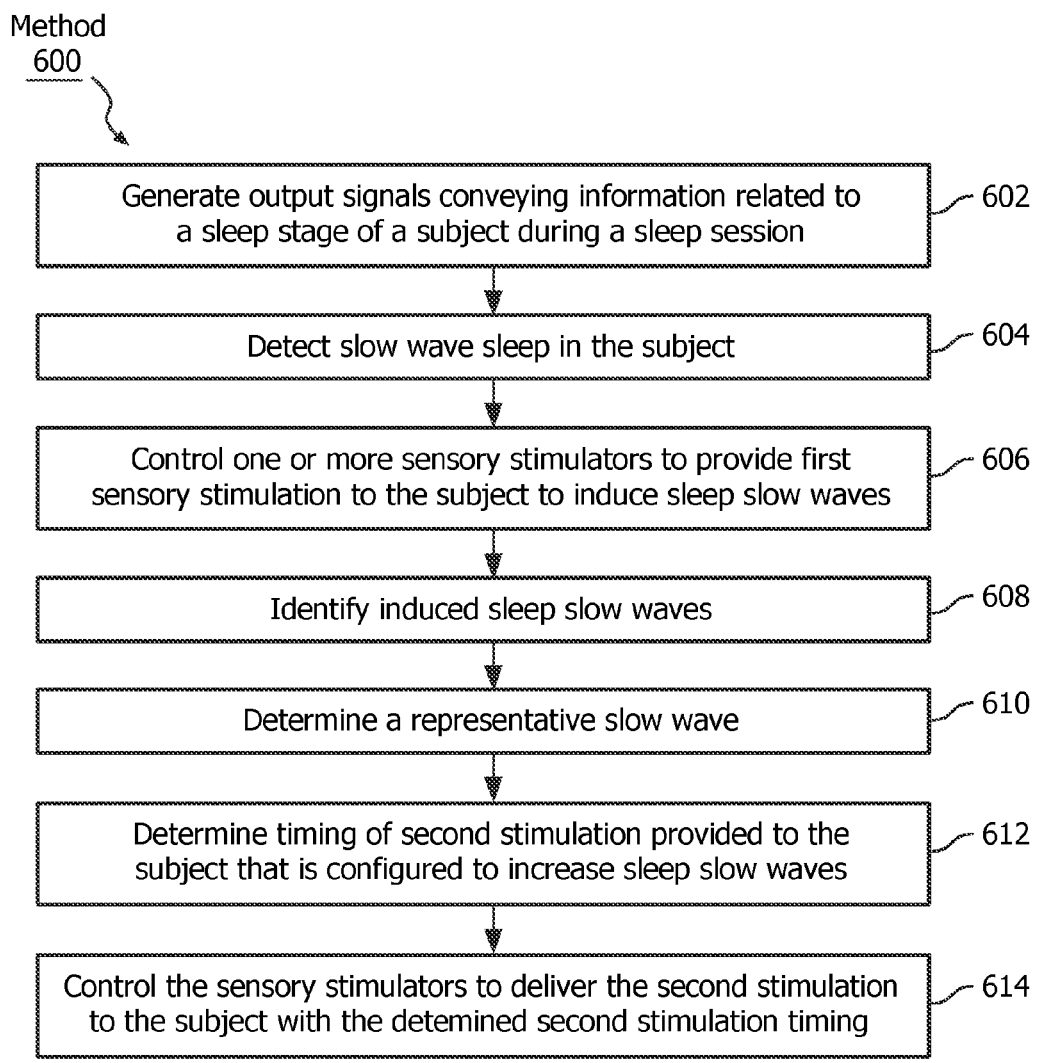
FIG. 6 illustrates a method for determining timing of sensory stimulation provided to a subject to increase sleep slow waves during a sleep session with a timing determination system.

FIG. 6 illustrates a method 600 for determining timing of sensory stimulation provided to a subject to increase sleep slow waves during a sleep session with a timing determination system. As described above, slow wave sleep may be and/or include stage N3 sleep (e.g., according to the new denomination), S4 sleep (e.g., according to the former denomination), deep sleep and/or other slow wave sleep. In some embodiments, slow wave sleep, stage N3 sleep, S4 sleep, and/or deep sleep may all refer to the same type of sleep. The system comprises one or more sensory stimulators, one or more sensors, one or more processors, and/or other components. The one or more processors are configured to execute computer program modules. The computer program modules comprise a slow wave sleep detection module, a probing stimulation module, an identification module, a combination module, a stimulation timing module, and/or other modules. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, output signals conveying information related to a sleep stage of the subject during a sleep session are generated. In some embodiments, operation 602 is performed by one or more sensors the same as or similar to sensors 18 (shown in FIG. 1 and described herein).

At an operation 604, slow wave sleep is detected in the subject. Slow wave sleep is detected based on the output signals. In some embodiments, operation 604 is performed by a computer program module the same as or similar to slow wave sleep detection module 30 (shown in FIG. 1 and described herein).

At an operation 606, the one or more sensory stimulators are controlled to provide first sensory stimulation to the subject to induce sleep slow waves. The first sensory stimulation may be probing sensory stimulation and/or other stimulation. The first sensory stimulation may comprise three or more individual stimuli delivered to the subject with random intervals of time between the individual stimuli. In some embodiments, the random intervals of time between the individual stimuli may be at least two seconds. In some embodiments, the random intervals of time may be at least 3 seconds. In some embodiments, the random intervals of time may be at least 4 seconds. In some embodiments, operation 606 is performed by a computer program module the same as or similar to probing stimulation module 32 (shown in FIG. 1 and described herein).

In some embodiments, the following operations 608 and 610 may be combined into a single operation. The single operation may be and/or include performing a time locked average and/or other operations on the EEG signal. Individual induced slow waves may be aligned in time (with respect to the timing of the individual probing stimuli) and combined (e.g., averaged) to obtain a representative evoked sleep slow wave (e.g., this may be a typical slow wave which has a higher signal-to-noise ratio because of the averaging) which is used to obtain a higher-confidence estimate of the slow wave duration. The alignment of the slow waves is done according to the timing of the individual stimuli (e.g., tones) in the probing stimulation. The process is illustrated in FIG. 3A as described above.

At an operation 608, induced sleep slow waves may be identified (though this may not be required as a separate step for time locked averaging). The induced sleep slow waves may be identified based on the output signals. In some embodiments, operation 608 is performed by a computer program module the same as or similar to identification module 34 (shown in FIG. 1 and described herein).

At an operation 610, a representative slow wave is determined. The representative slow wave is determined based on a combination of the identified induced sleep slow waves (e.g., time locked averaging). The representative slow wave may include a first electrical activity peak and a second electrical activity peak. In some embodiments, operation 610 is performed by a computer program module the same as or similar to combination module 36 (shown in FIG. 1 and described herein).

At an operation 612, timing of second stimulation provided to the subject is determined. The second stimulation is configured to increase sleep slow waves. The timing of the second stimulation is determined based on the representative slow wave. The timing of the second stimulation may be determined based on an amount of time between the first electrical activity peak and the second electrical activity peak of the representative slow wave. In some embodiments, the timing of the second stimulation comprises a regular, repeating interval of time between individual stimuli delivered to the subject. In some embodiments, operation 612 is performed by a computer program module the same as or similar to stimulation timing module 38 (shown in FIG. 1 and described herein).

At an operation 614, the sensory stimulators are controlled to deliver the second stimulation to the subject with the determined second stimulation timing. In some embodiments, operation 614 is performed by a computer program module the same as or similar to control module 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to determine timing of sensory stimulation provided to a subject to increase sleep slow waves during a sleep session, the system comprising:
   one or more sensory stimulators configured to provide sensory stimuli to the subject during the sleep session;
   one or more sensors configured to generate output signals conveying information related to a sleep stage of the subject during the sleep session; and
   one or more physical computer processors configured by machine-readable instructions to execute computer program modules, the computer program modules comprising:
      a slow wave sleep detection module configured to detect slow wave sleep in the subject based on the output signals;
      a probing stimulation module configured to, responsive to detection of slow wave sleep, control the one or more sensory stimulators to provide first sensory stimulation to the subject to induce sleep slow waves, the first sensory stimulation comprising one or more individual probing stimuli;
      a combination module configured to determine a representative slow wave, the representative slow wave determined based on the induced sleep slow waves, the representative slow wave comprising a combination of individual induced sleep slow waves evoked by the one or more individual probing stimuli that have been aligned in time with respect to timing of the one or more individual probing stimuli; and
      a stimulation timing module configured to determine timing of second stimulation provided to the subject, the second stimulation configured to increase sleep slow waves in the subject during the sleep session, the timing determination based on the representative slow wave.

2. The system of claim 1, further comprising a control module configured to control the one or more sensory stimulators to deliver the second stimulation to the subject with the timing determined by the stimulation timing module.

3. The system of claim 1, wherein the combination module is configured such that the representative slow wave includes a first electrical activity peak and a second electrical activity peak, and wherein the stimulation timing module is configured to determine the timing of the second stimulation based on an amount of time between the first electrical activity peak and the second electrical activity peak.

4. The system of claim 1, wherein the probing stimulation module is configured such that the first sensory stimulation comprises three or more individual probing stimuli delivered to the subject with random intervals of time between the individual probing stimuli, and wherein the random intervals of time between the individual probing stimuli are at least two seconds.

5. The system of claim 1, wherein the stimulation timing module is configured such that the timing of the second stimulation comprises a regular, repeating interval of time between individual stimuli delivered to the subject.

6. A method for determining timing of sensory stimulation provided to a subject to increase sleep slow waves during a sleep session with a timing determination system, the system comprising one or more sensory stimulators, one or more sensors, and one or more physical computer processors, the one or more processors configured by machine-readable instructions to execute computer program modules, the computer program modules comprising a slow wave sleep detection module, a probing stimulation module, a combination module, and a stimulation timing module, the method comprising:
   generating output signals conveying information related to a sleep stage of the subject during the sleep session with the one or more sensors;
   detecting, with the slow wave sleep detection module, slow wave sleep in the subject based on the output signals;
   responsive to detection of slow wave sleep, controlling the one or more sensory stimulators, with the probing stimulation module, to provide first sensory stimulation to the subject to induce sleep slow waves, the first sensory stimulation comprising one or more individual probing stimuli;

determining, with the combination module, a representative slow wave, the representative slow wave determined based on the induced sleep slow waves, the representative slow wave comprising a combination of individual induced sleep slow waves evoked by the one or more individual probing stimuli that have been aligned in time with respect to timing of the one or more individual probing stimuli; and determining, with the stimulation timing module, timing of second stimulation provided to the subject, the second stimulation configured to increase sleep slow waves in the subject during the sleep session, the timing determination based on the representative slow wave.

7. The method of claim 6, further comprising controlling, with a control module executed by the one or more physical computer processors, the one or more sensory stimulators to deliver the second stimulation to the subject with the timing determined by the stimulation timing module.

8. The method of claim 6, wherein the representative slow wave includes a first electrical activity peak and a second electrical activity peak, and wherein determining the timing of the second stimulation is based on an amount of time between the first electrical activity peak and the second electrical activity peak.

9. The method of claim 6, wherein the first sensory stimulation comprises three or more individual probing stimuli delivered to the subject with random intervals of time between the individual probing stimuli, and wherein the random intervals of time between the individual probing stimuli are at least two seconds.

10. The method of claim 6, wherein the timing of the second stimulation comprises a regular, repeating interval of time between individual stimuli delivered to the subject.

11. A system configured to determine timing of sensory stimulation provided to a subject to increase sleep slow waves during a sleep session, the system comprising:

means for providing sensory stimuli to the subject during the sleep session;

means for generating output signals conveying information related to a sleep stage of the subject during the sleep session;

means for detecting slow wave sleep in the subject based on the output signals;

means for, responsive to detection of slow wave sleep, controlling the means for providing sensory stimuli to provide first sensory stimulation to the subject to induce sleep slow waves, the first sensory stimulation comprising one or more individual probing stimuli;

means for determining a representative slow wave, the representative slow wave determined based on the induced sleep slow waves, the representative slow wave comprising a combination of individual induced sleep slow waves evoked by the one or more individual probing stimuli that have been aligned in time with respect to timing of the one or more individual probing stimuli; and means for determining timing of second stimulation provided to the subject, the second stimulation configured to increase sleep slow waves in the subject during the sleep session, the timing determination based on the representative slow wave.

12. The system of claim 11, further comprising means for controlling the means for providing sensory stimuli to deliver the second stimulation to the subject with the timing determined by the means for determining timing of the second stimulation.

13. The system of claim 11, wherein the means for determining a representative slow wave is configured such that the representative slow wave includes a first electrical activity peak and a second electrical activity peak, and wherein the means for determining timing of the second stimulation is configured to determine the timing of the second stimulation based on an amount of time between the first electrical activity peak and the second electrical activity peak.

14. The system of claim 11, wherein the means for controlling the means for providing sensory stimuli to provide first sensory stimulation is configured such that the first sensory stimulation comprises three or more individual probing stimuli delivered to the subject with random intervals of time between the individual probing stimuli, and wherein the random intervals of time between the individual probing stimuli are at least two seconds.

15. The system of claim 11, wherein the means for determining the timing of the second stimulation is configured such that the timing of the second stimulation comprises a regular, repeating interval of time between individual stimuli delivered to the subject.

* * * * *